(12) United States Patent
Izumo

(10) Patent No.: US 10,548,539 B2
(45) Date of Patent: Feb. 4, 2020

(54) X-RAY CT APPARATUS AND SCANNING METHOD

(71) Applicant: HITACHI, LTD., Tokyo (JP)

(72) Inventor: Hirohisa Izumo, Tokyo (JP)

(73) Assignee: HITACHI, LTD., Tokyo (JP)

( * ) Notice: Subject to any disclaimer, the term of this patent is extended or adjusted under 35 U.S.C. 154(b) by 202 days.

(21) Appl. No.: 15/535,859

(22) PCT Filed: Jan. 13, 2016

(86) PCT No.: PCT/JP2016/050755
§ 371 (c)(1),
(2) Date: Jun. 14, 2017

(87) PCT Pub. No.: WO2016/117418
PCT Pub. Date: Jul. 28, 2016

(65) Prior Publication Data
US 2017/0347974 A1 Dec. 7, 2017

(30) Foreign Application Priority Data

Jan. 23, 2015 (JP) ................. 2015-010871

(51) Int. Cl.
*A61B 6/03* (2006.01)
*A61B 6/04* (2006.01)
(Continued)

(52) U.S. Cl.
CPC ............ *A61B 6/032* (2013.01); *A61B 6/0407* (2013.01); *A61B 6/461* (2013.01); *A61B 6/468* (2013.01);
(Continued)

(58) Field of Classification Search
CPC ....... A61B 6/468; A61B 6/462; A61B 6/5205; A61B 6/412; A61B 6/032; G01N 23/046
See application file for complete search history.

(56) References Cited

U.S. PATENT DOCUMENTS

2011/0150173 A1* 6/2011 Shinno ................. A61B 6/032
378/5

FOREIGN PATENT DOCUMENTS

| CN | 1846622 A | 10/2006 |
|---|---|---|
| JP | 2003-190145 | 7/2003 |

(Continued)

OTHER PUBLICATIONS

International Search Report dated Mar. 22, 2016 in connection with PCT/JP2016/050755.
(Continued)

*Primary Examiner* — Don K Wong
(74) *Attorney, Agent, or Firm* — Cooper & Dunham LLP

(57) ABSTRACT

According to an X-ray CT apparatus and a scanning method of the present invention, in order to efficiently create an image used for diagnosis, an operator selects a desired part from a part selection GUI before main scanning by using an ROI object imitating a shape of each part, held in a storage device, and thus the ROI object can be disposed on a scanogram image, in which setting information corresponding to a part is set for the ROI object in advance, a region of interest associated with the part is set, main scanning is performed under conditions associated with the set region of interest, and an image is reconstructed on the basis of X-ray information obtained through the main scanning.

13 Claims, 19 Drawing Sheets

(51) Int. Cl.
    *A61B 6/00*    (2006.01)
    *G01N 23/046*    (2018.01)
(52) U.S. Cl.
    CPC .............. *A61B 6/5205* (2013.01); *A61B 6/54* (2013.01); *G01N 23/046* (2013.01)

(56) References Cited

FOREIGN PATENT DOCUMENTS

| | | |
|---|---|---|
| JP | 2003-230556 | 8/2003 |
| JP | 2003-275199 | 9/2003 |
| JP | 2005-261932 | 9/2005 |
| JP | 2006-158423 | 6/2006 |
| JP | 2006-312026 | 11/2006 |
| JP | 2009-50366 | 3/2009 |
| JP | 2009-72426 | 4/2009 |
| JP | 2013-479 | 1/2013 |

OTHER PUBLICATIONS

Sep. 27, 2019 Chinese official action (and machine translation thereof into English) in corresponding Chinese Patent Application No. 201680004215.8.

Japanese official action (and machine translation thereof into English) dated Sep. 10, 2019 in corresponding Japanese Patent Application No. 2016-570584.

\* cited by examiner

FIG.7
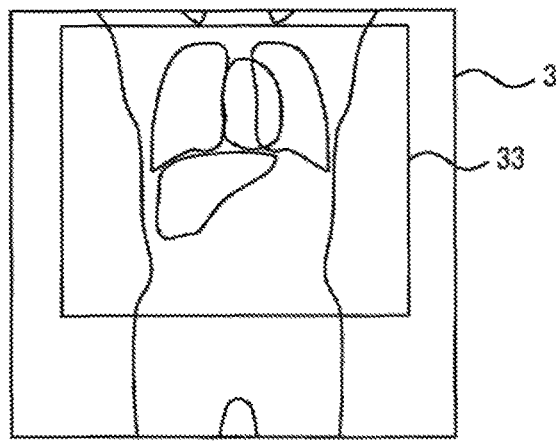
(a)
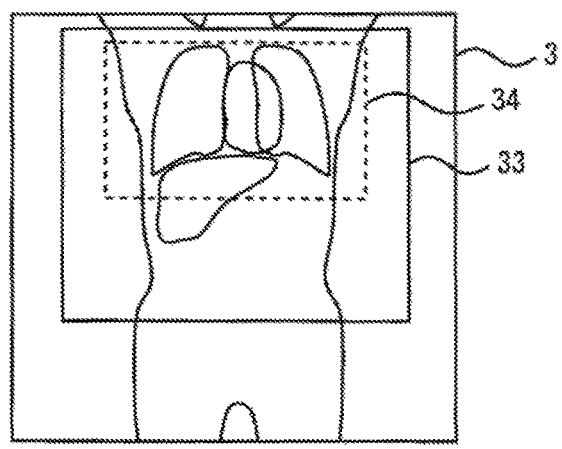
(b)
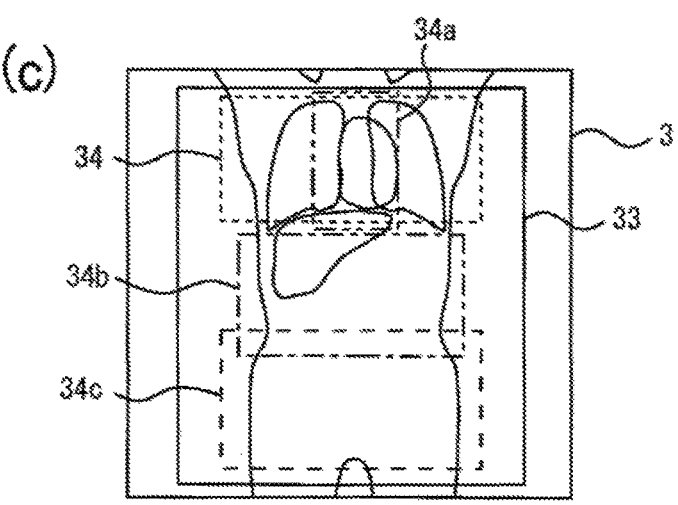
(c)

FIG.8
(a) PART SELECTION GUI
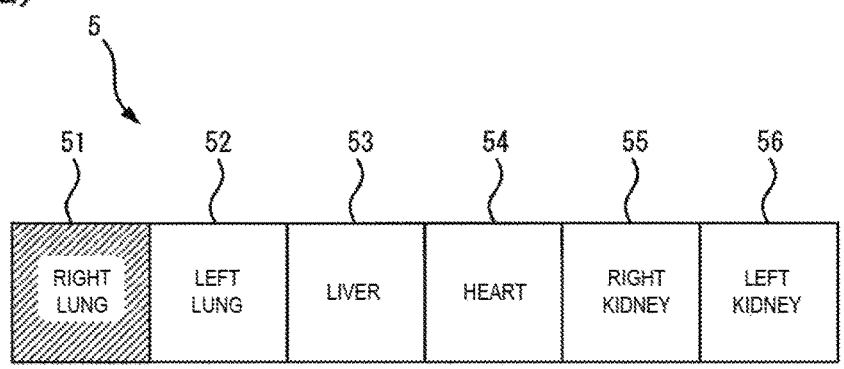
(b) 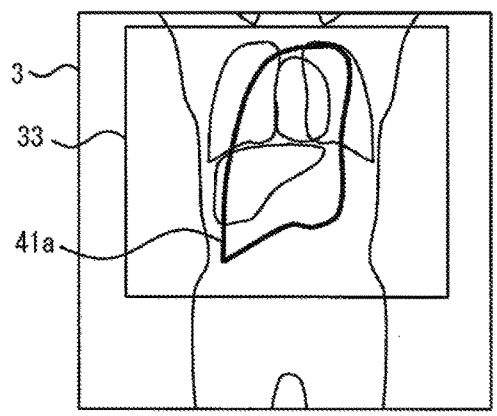 ADJUST (c) 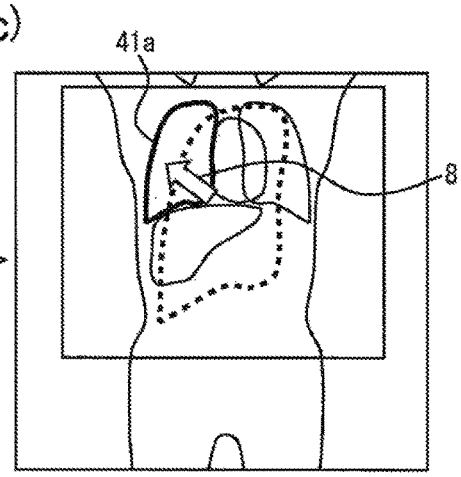

FIG.9
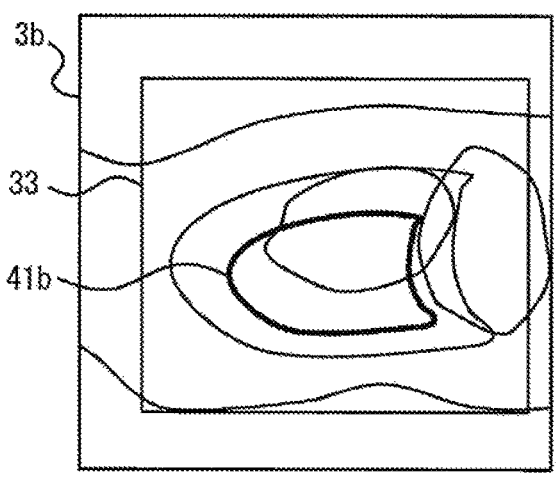
(a)
ADJUST
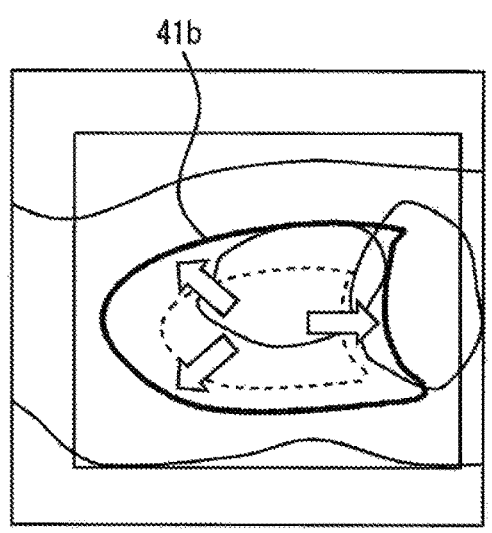
(b)

FIG.13
(a)
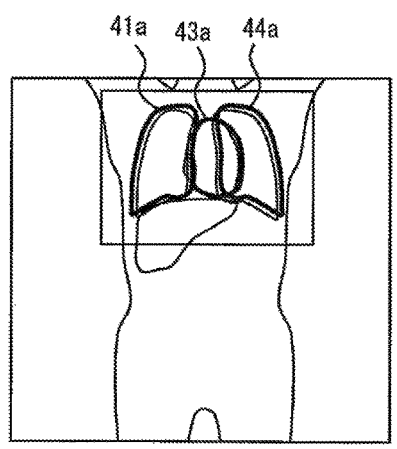
(b)
6 RECONSTRUCTION CONDITION TABLE
| MULTI-RECONSTRUCTION No. | IMAGE SLICE THICKNESS | FOV | FILTER | RECONSTRUCTION INTERVAL | WW/WL | IMAGE RANGE |
|---|---|---|---|---|---|---|
| 01 (FOR RIGHT LUNG) | 0.625 | 350 | 22 | 0.625 | 1500/-650 | 5.0~300.0mm |
| 02 (FOR LEFT LUNG) | 0.625 | 350 | 22 | 0.625 | 1500/-650 | 5.0~300.0mm |
| 03 (FOR HEART) | 0.625 | 150 | 71 | 5.000 | 600/80 | 10.0~145.0mm |

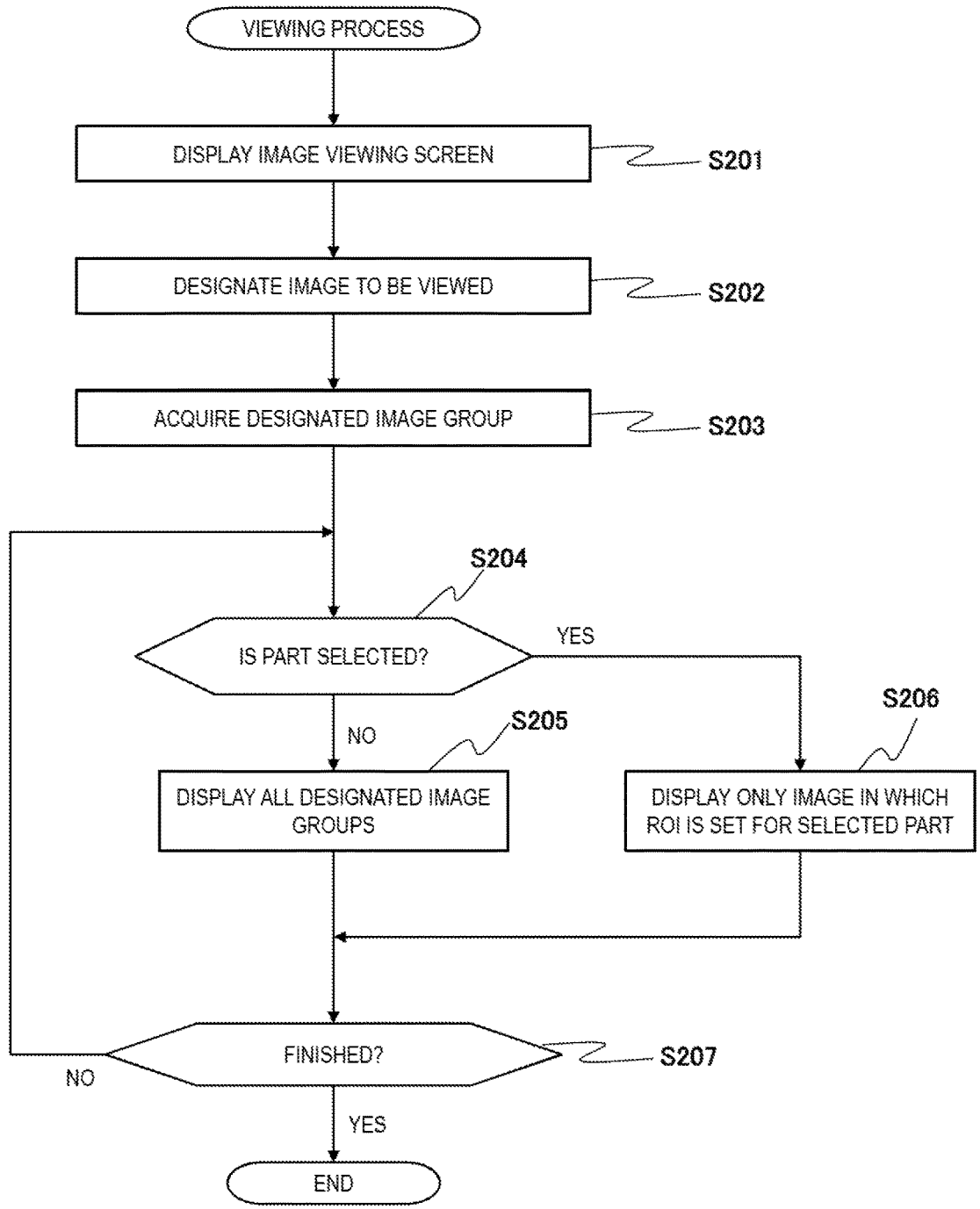

X-RAY CT APPARATUS AND SCANNING METHOD

TECHNICAL FIELD

The present invention relates to an X-ray CT apparatus and a scanning method, and particularly to a technique for efficiently scanning, reconstructing, and displaying an image.

BACKGROUND ART

In recent years, the number of images obtained through one scanning has been increased in an X-ray CT apparatus. The number of subjects scanned for a day has been increased due to improvement of throughput. Thus, a diagnostic reading doctor or the like observes a large number of images. In light of such a background, efforts have been made to efficiently perform image observation in a medical image display apparatus.

For example, in PTL 1, when a doctor observes tomographic images obtained through CT scanning while sequentially displaying the tomographic images, a function of adding a mark to an image suspected of including a lesion while viewing the images is provided. By using the function, an image at a position to which a mark is added can be easily read and displayed at any time, and thus work efficiency is improved. The medical image display apparatus disclosed in PTL 1 additionally has a function of automatically setting a careful inspection range on the basis of the image position to which the mark is added, and thus it is possible to simplify an operation.

CITATION LIST

Patent Literature

PTL 1: JP-A-2003-275199

SUMMARY OF INVENTION

Technical Problem

However, in the medical image display apparatus disclosed in PTL 1, a diagnostic reading doctor or the like is required to read a large number of obtained through CT scanning one by one from a first image to a last image in order to add a mark. This image reading is required to be performed for dozens of people a day. Thus, it is necessary to efficiently create or view an image used for diagnosis.

The present invention has been made in light of the above-described problem, and an object thereof is to provide an X-ray CT apparatus and a scanning method capable of efficiently creating an image used for diagnosis.

Solution to Problem

According to the present invention, in order to achieve the above-described object, there is provided an X-ray CT apparatus including an X-ray irradiation unit that irradiates X-rays from each direction around a subject; an X-ray detection unit that detects X-rays having been transmitted through the subject; a scanogram image creation unit that relatively moves positions of the subject and the X-ray irradiation unit in a body axis direction in a state in which an X-ray irradiation direction is fixed, so as to create a scanogram image through scanning; a storage unit that holds a plurality of objects indicating regions of interest associated with parts; a region-of-interest setting unit that disposes an object on the scanogram image so as to set a region of interest associated with a part; and an image reconstruction unit that performs main scanning, and reconstructs an image including the region of interest under conditions corresponding to the part on the basis of X-ray information obtained through the main scanning.

According to the present invention, there is provided a scanning method for an X-ray CT apparatus which irradiates X-rays from each direction around a subject, and detects X-rays having been transmitted through the subject, the method including a step of moving a position of the subject in a body axis direction in a state in which an X-ray irradiation direction is fixed, so as to create a scanogram image; a step of disposing object indicating a region of interest associated with a part on the scanogram image so as to set the region of interest associated with the part; and a step of performing main scanning, and reconstructing an image including the region interest under conditions corresponding to the part on the basis of X-ray information obtained through the main scanning.

Advantageous Effects of Invention

According to the present invention, it is possible to provide an X-ray CT apparatus and a scanning method capable of efficiently creating an image used for diagnosis.

BRIEF DESCRIPTION OF DRAWINGS

FIG. 3 is a diagram illustrating a reconstructed image range and a reconstruction FOV size determined by an ROI object 41a.

FIG. 7 illustrates setting examples of a scanning range and a reconstruction range of the related art.

FIG. 8 illustrates setting examples (ROI setting examples) of a scanning range and a reconstruction range of the present invention, in which FIG. 8(a) illustrates a state in which a "right lung" is selected on the part selection GUI 5, FIG. 8(b) illustrates a state in which a right lung ROI 41a is placed on a scanogram image 3, and FIG. 8(c) illustrates a state in which a size and a position of the right lung ROI 41a are adjusted.

FIG. 9 illustrates an example in which a right lung ROI 41b is disposed on a LAT direction scanogram image.

FIG. 10 is a state in which a center mark 47 is set in the right lung ROI 41a.

FIG. 13 illustrates an example of setting a plurality of regions of interest (ROI objects) in the same scanning range, and an example of a reconstruction conditions table 6 defining reconstruction conditions set in this case.

FIG. 16 is a flowchart illustrating a flow of a viewing process performed after scanning is finished.

DESCRIPTION OF EMBODIMENTS

Figure 1:
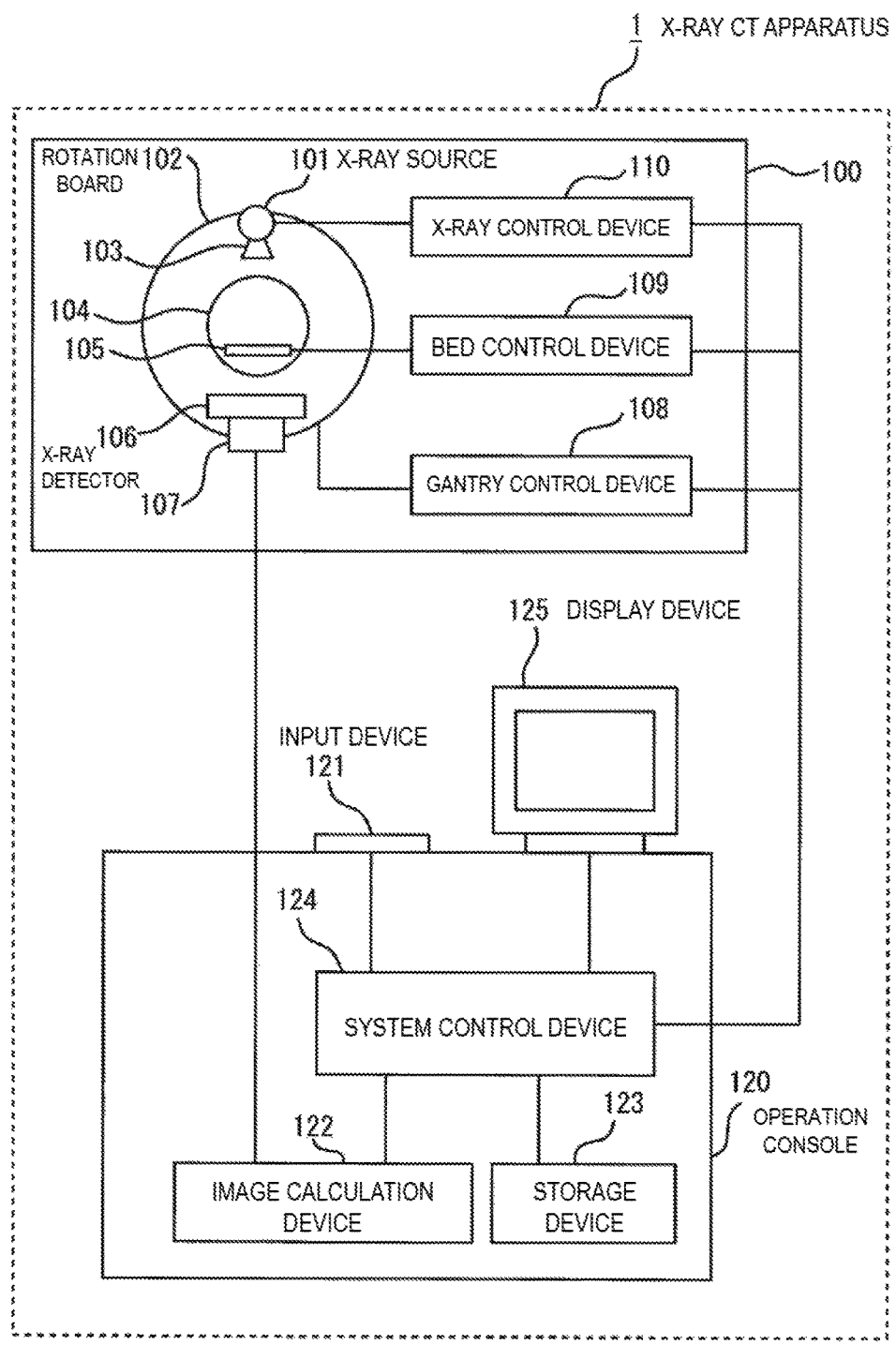
FIG. 1 is a diagram illustrating the entire configuration of an X-ray CT apparatus 1.

According to the present invention, an X-ray CT apparatus includes an X-ray irradiation unit that irradiates X-rays from each direction around a subject; an X-ray detection unit that detects X-rays having been transmitted through the subject; a scanogram image creation unit that relatively moves positions of the subject and the X-ray irradiation unit in a body axis direction in a state in which an X-ray irradiation direction is fixed, so as to create a scanogram image through scanning; a storage unit that holds a plurality of objects indicating parts; a region-of-interest setting unit that disposes an object on the scanogram image so as to set a region of interest associated with a part; and an image reconstruction unit that performs main scanning, and reconstructs an image including the region of interest under conditions corresponding to the part on the basis of X-ray information obtained through the main scanning.

A shape of the object may be a shape corresponding to a part.

The X-ray CT apparatus may further include an operation input unit that inputs an operation of adjusting a shape of the object.

A reconstruction field of view range in a slice section may be determined on the basis of a shape of the region of interest.

The X-ray CT apparatus may further include a setting information input unit that sets setting information including at least reconstruction conditions for each object, in which the image reconstruction unit reconstructs an image on the basis of the setting information.

The X-ray CT apparatus may further include a notification unit that performs a notification of a scanning position or a scanning part in a case where a position including the region of interest is scanned in the main scanning.

The image reconstruction unit may sequentially reconstruct tomographic images during execution of main scanning, and the X-ray CT apparatus may further include a display unit that arranges and displays the scanogram image and the tomographic images in real time, and displays scanning positions of the tomographic images on the scanogram image.

The display unit may display a position of the region of interest in a case where the region of interest is included in a currently displayed tomographic image.

The X-ray CT apparatus may further include a mark adding unit that adds a mark to a currently displayed tomographic image.

The object may be associated with information for designating a processing program which automatically activated after an image is reconstructed, and the X-ray CT apparatus may further include a program activation unit that activates the processing program after an image is reconstructed.

The X-ray CT apparatus may further include a storage unit that stores a reconstructed image group; a part selection unit that selects a part; and an image viewing processing unit that extracts and acquires an image including a selected part from the storage unit, and displays the acquired image under display conditions set for a region of interest associated with the part.

The X-ray CT apparatus may further include a storage unit that stores a reconstructed image group; and a part-basis display unit that acquires images from the storage unit, and arranges and displays the images for each part.

The X-ray CT apparatus may further include a storage unit that stores a reconstructed image group in correlation with information regarding the date and time which the image group is scanned; and a time-series display unit that acquires images of the same patient which are scanned at another date and time and include a specific region of interest from the storage unit, and that arranges and displays the images in a time series.

According to the present invention, a scanning method for an X-ray CT apparatus which irradiates X-rays from each direction around a subject, and detects X-rays having been transmitted through the subject, includes a step of moving a position of the subject in a body axis direction in a state in which an X-ray irradiation direction is fixed, so as to create a scanogram image through scanning; a step of disposing an object indicating a region of interest associated with a part on the scanogram image so as to set the region of interest associated with the part; and a step of performing main scanning, and reconstructing an image including the region of interest under conditions corresponding to the part on the basis of X-ray information obtained through the main scanning.

Hereinafter, embodiments of the present invention will be described in detail with reference to the drawings.

First, with reference to FIG. 1, a description will be made of the entire configuration of an X-ray CT apparatus 1.

As illustrated in FIG. 1, the X-ray CT apparatus 1 includes a scan gantry portion 100, a bed 105, and an operation console 120. The scan gantry portion 100 is a device which irradiates a subject with Z-rays and detects X-rays transmitted through the subject. The operation console 120 is a device which controls each constituent element of the scan gantry portion 100, and acquires transmitted X-ray data measured by the scan gantry portion 100 so as to generate an image. The bed 105 is a device on which the subject is laid and is mounted and which carries the subject into and out of an X-ray irradiation range of the scan gantry portion 100.

The scan gantry portion 100 includes an X-ray source (X-ray irradiation unit) 101, a rotation board 102, a collimator 103, an X-ray detector 106, a data collecting device 107, a gantry control device 108, a bed control device 109, and an X-ray control device 110.

The operation console 120 includes an input device 121, an image calculation device 122, a storage device 123, a system control device 124, and a display device 125.

The rotation board 102 of the scan gantry portion 100 is provided with an opening 104, and the X-ray source 101 and the X-ray detector 106 are disposed to oppose each other with the opening 104 interposed therebetween. A subject mounted on the bed 105 is inserted into the opening 104. The rotation board 102 is rotated around the subject by a driving force which is transmitted from a rotation board driving device via a driving transmission system. The rotation board driving device is controlled by the gantry control device 108.

The X-ray source 101 is controlled by the X-ray control device 110 so as to apply X-rays with a predetermined intensity continuously or intermittently. The X-ray control device 110 controls an X-ray tube voltage applied or supplied to the X-ray source 101 and an X-ray tube current supplied thereto according to an X-ray tube voltage and an X-ray tube current determined by the system control device 124 the operation console 120.

The collimator 103 is provided an X-ray irradiation outlet of the X-ray source 101. The collimator 103 restricts an irradiation range of X-rays irradiated from the X-ray source 101. For example, an irradiation range is shaped into a cone beam (conical or pyramidal beam). An aperture width of the collimator 103 is controlled by the system control device 124.

The X-rays, irradiated from the X-ray source 101, passing through the collimator 103, and transmitted through the subject, are incident to the X-ray detector 106.

The X-ray detector 106 is detector in which for example, X-ray detection element groups each formed of a scintillator and a photodiode are two-dimensionally arranged in a channel direction (rotation direction) and a column direction (body axis direction). The X-ray detector 106 is disposed to oppose the X-ray source 101 via the subject. The X-ray detector 106 detects a dose of X-rays irradiated from the X-ray source 101 and transmitted through the subject, and outputs the dose to the data collecting device 107.

The data collecting device 107 collects an X-ray dose detected by each X-ray detection element of the X-ray detector 106, converts the X-ray dose into a digital signal, and sequentially outputs the digital signal to the image calculation device 122 of the operation console 120 as transmitted X-ray data.

The image calculation device 122 acquires the transmitted X-ray data which is input from the data collecting device 107, and performs pre-processing such as logarithmic conversion and sensitivity correction on the transmitted X-ray data so as to create projection data which is necessary in reconstruction. The image calculation device 122 reconstructs an image such as a tomographic image drawing the inside of the subject by using the generated projection data. The system control device 124 stores an image data reconstructed by the image calculation device 122 in the storage device 123, and also displays the image data on the display device 125.

The system control device 124 is a computer provided with a central processing unit (CPU), a read only memory (ROM), a random access memory (RAM), and the like. The storage device 123 is a data recording device such as a hard disk, and stores in advance programs or data for realizing a function of the X-ray CT apparatus 1.

In the present invention, the system control device 124 receives a region of interest (ROI) set on a scanogram image which is obtained through positioning scanning before main scanning. It is assumed that an ROI is associated with a part, and scanning or reconstruction conditions are set for each part. The system control device 124 performs control so that main scanning and image reconstruction are performed under conditions corresponding to the set ROI. Details of this process will be described later.

The storage device 123 holds various pieces of information regarding setting of a region of interest (ROI). For example, the storage device 123 stores ROI tables 41*a* and 41*b* (refer to FIG. 2) for setting ROI objects 41*a*, 41*b*, 42*a*, 42*b*, 43*a*, 43*b*, . . . which are objects indicating parts to be associated with the parts. The storage device 123 stores various pieces of setting information (refer to FIG. 4) for the respective ROI objects 41*a*, 41*b*, 42*a*, 42*b*, 43*a*, 43*b*, . . . . The storage device 123 stores projection data acquired by the data collecting device 107, or an image reconstructed by the image calculation device 122.

The display device 125 is constituted of a display device such as a liquid crystal panel or a CRT monitor, and a logic circuit for performing a display process in conjunction with the display device, and is connected to the system control device 124. The display device 125 displays an image output from the image calculation device 122, and various pieces of information treated by the system control device 124.

The input device 121 is formed of, for example a pointing device such as a keyboard or a mouse, a numerical keypad, and various switch buttons, and outputs various instructions or information input by an operator, to the system control device 124. An operator operates the X-ray CT apparatus 1 in an interaction manner by using the display device 125 and the input device 121. The input device 121 may be a touch panel type input device which is integrally formed with a display screen of the display device 125.

The bed 105 includes a top plate on which a subject is laid and mounted, a vertical movement device, and a top plate driving device. The top plate is moved up and down, moved in a front-and-rear direction along the body axis direction, or moved in a leftward-and-rightward direction which is perpendicular to a body axis and is parallel to a floor surface, under the control of the bed control device 109. During scanning, the bed control device 109 moves the top plate at a bed movement speed and in a movement direction determined by the system control device 124.

Next, with reference to FIGS. 2 to 4, a description will be made of a ROI object used for a scanning process of the present invention.

Figure 2:
FIG. 2 is a diagram illustrating examples of ROI tables 4a and 4b in which ROI objects and shapes thereof are set.

As illustrated in FIG. 2, in the X-ray CT apparatus 1, the storage device 123 holds the ROI tables 4*a* and 4*b* in which a part is associated with an ROI object. FIG. 2(*a*) illustrates an example of the ROI table 4*a* storing the ROI objects 41*a*, 42*a*, 43*a*, . . . used for a postero-anterior (PA) direction scanogram image, and FIG. 2(*b*) illustrates an example of the ROI table 4*b* storing the ROI objects 41*b*, 42*b*, 43*b*, . . . used for a lateral (LAT) direction scanogram image. The PA direction image is a scanning image from the front of a subject, the LAT direction image is a scanning image from the side of the subject.

The ROI objects 41*a*, 41*b*, 42*a*, 42*b*, 43*a*, 43*b*, . . . are graphical user interfaces (GUIs) for visually indicating regions of interest (ROIs). It is assumed that each of the ROI objects 41*a*, 41*b*, . . . indicates a part, and is associated with the part. Each of the ROI objects 41*a*, 41*b*, . . . has a defined shape imitating a shape of the part. The parts include, for example, the right lung, the liver, the heart, the left lung, the right kidney, the left kidney, and other organs. A size, a position, an angle, and the like of each of the ROI objects 41*a*, 41*b*, . . . are preferably adjusted by the operator depending on a size, an angle, or the like of a scanogram image.

The ROI objects 41*a*, 41*b*, . . . are used for setting scanning conditions and reconstruction conditions. Each of the ROI objects 41*a*, 41*b*, . . . is uniquely associated with a part, and various pieces of setting information such as reconstruction conditions or display conditions are set for each of the ROI objects 41*a*, 41*b*, . . . in advance. If the operator disposes the ROI objects 41*a*, 41*b*, . . . on a scanogram image which is scanned for positioning, the system control device 124 determines scanning ranges corresponding to positions of the ROI objects 41*a*, 41*b*, . . . , reads setting information associated with the disposed ROI objects 41*a*, 41*b*, . . . , and sets reconstruction conditions (an image slice thickness, a reconstruction interval, a reconstruction filter, a reconstruction FOV, and the like) corresponding to the setting information.

In a case where conditions other than a scanning range or a reconstruction FOV are set to be associated with parts (the ROI objects 41*a*, 41*b*, . . . ) in advance, various conditions (scanning conditions, reconstruction conditions, display parameters, and the like) are set according to the set information.

Consequently, if the operator operates the mouse, and disposes the ROI objects 41*a*, 41*b*, . . . indicating parts at position desired to be of interest on the scanogram image, the system control device 124 immediately sets scanning ranges corresponding to shapes of the ROI objects 41*a*, 41*b*, . . . or reconstruction conditions and display parameters corresponding to the parts, and can thus rapidly transition to a scanning process, an image reconstruction process, and a viewing process, and can also omit a condition setting operation or the like in each process.

Figure 3:
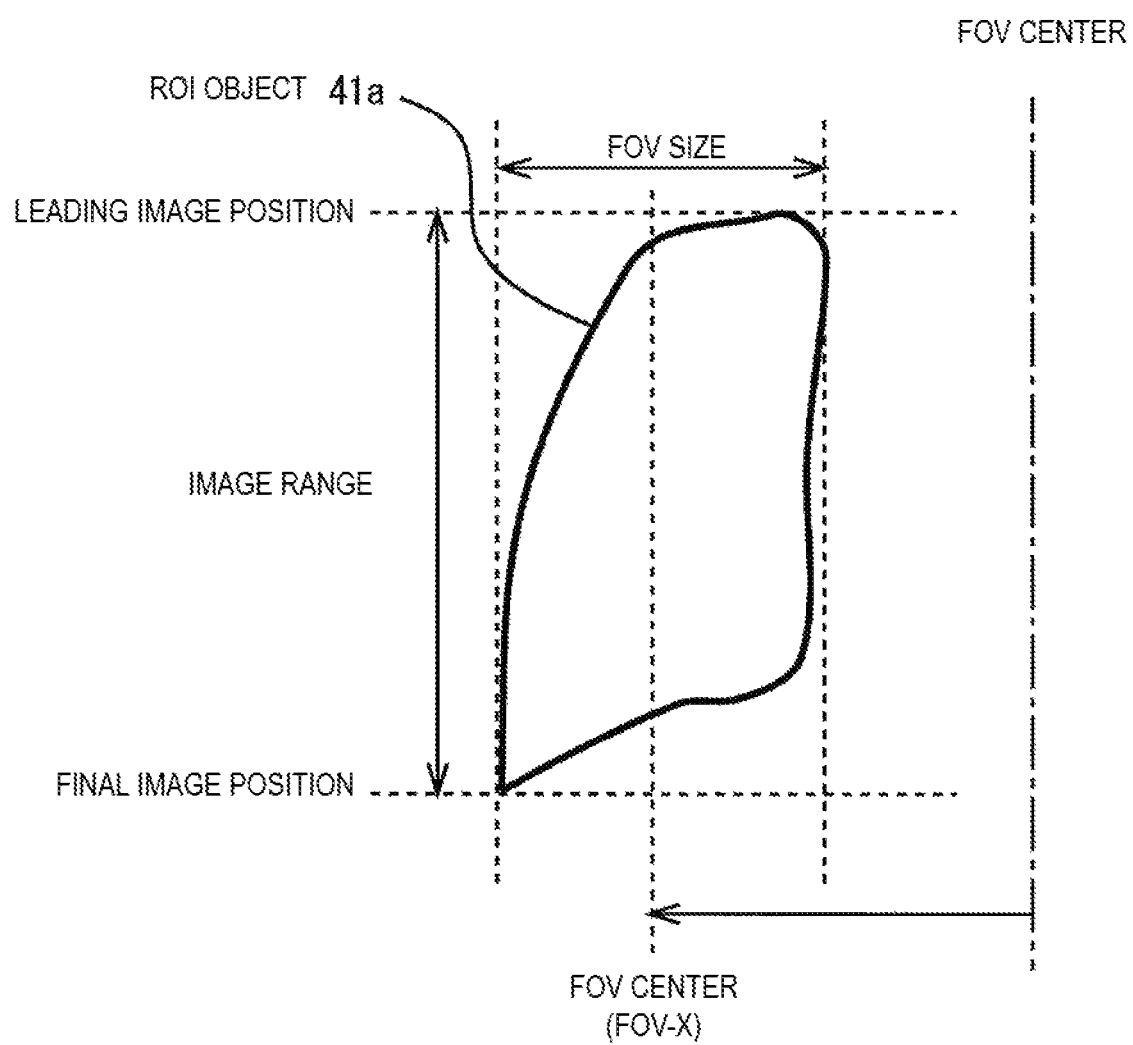

FIG. 3 is a diagram illustrating correspondence between respective portions of a PA direction right lung ROI object 41*a* and reconstruction conditions. A longitudinal width of the PA direction right lung ROI object 41*a* is an image range in a Z direction (body axis direction), an upper end corresponds to a leading image position, and a lower end corresponds to a final image position. There is case where an upper end corresponds to a final image position, and a lower end corresponds to a leading image position, depending on a scanning direction. A transverse width of the ROI object 41*a* corresponds to an FOV size, and a central line between a left end and a right end is assumed to be the FOV center. FIG. 3 illustrates the ROI object 41*a* for a PA direction scanogram image (a scanogram image scanned by disposing a tubular bulb in front of a subject), and thus an FOV range or the FOV center is determined with respect to an X direction (body width direction).

Also for a LAT direction ROI object, in the same manner as in FIG. 3, an FOV range, an image range (a leading image position and a final image position), and the like are determined depending on a longitudinal width and a transverse width of each ROI object. A transverse direction of the LAT direction ROI object corresponds to the body axis direction, and a vertical (longitudinal) direction of the ROI object corresponds to a body thickness direction.

A processing program (an analysis application or the like) which is automatically activated after an image is reconstructed, or various pieces of setting information, for example, display parameters such as a window width (WW) and a window level (WL) are preferably set to be associated with each ROI object. The processing program automatically activated after an image is reconstructed is, for example, an analysis application appropriate for a part, or an image processing application for performing image processing such as extraction of a specific part.

Figure 4:
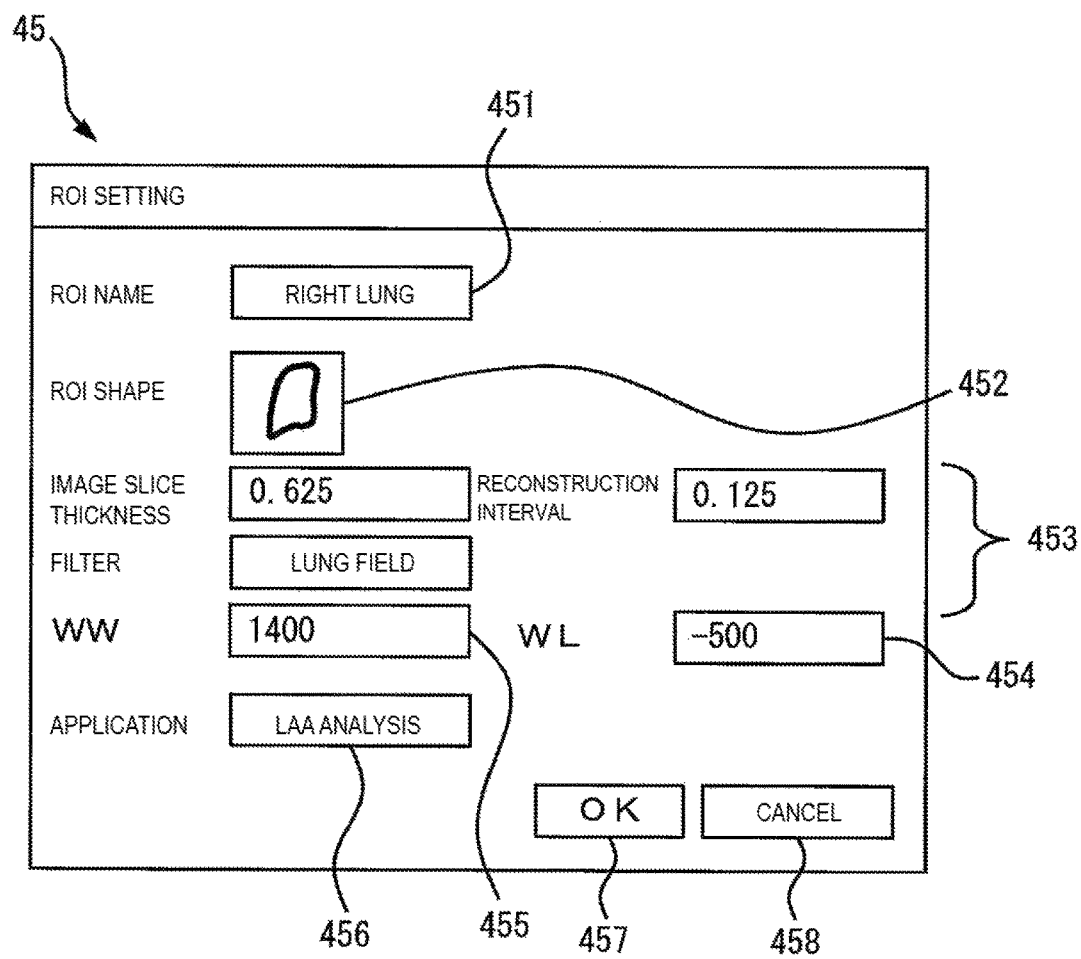
FIG. 4 illustrates an example of an ROI setting screen 45 for setting ROI setting information.

FIG. 4 illustrates an example of a ROI setting screen 45.

As illustrated in FIG. 4, the ROI setting screen 45 includes an ROI name input column 451, an ROI shape designation column 452, a reconstruction condition input column 453 for setting reconstruction conditions such as an image slice thickness, a reconstruction interval, and a reconstruction filter, display parameter input columns 454 and 455 for inputting display parameters such as a window width (WW) and a window level (WL), an application designation column 456 for designating a processing program (application) automatically activated after an image is reconstructed, an "OK" button 457 which is operated when the content input to the respective setting item input columns 451 to 456 in the storage device 123 as ROI setting information, a "cancel" button 458 operated when an ROI setting operation is canceled and the ROI setting screen 45 is finished, and the like.

The operator may set various conditions correlated with each of the ROI objects 41*a*, 41*b*, . . . by inputting desired values to the respective columns 451 to 456 by using the input device 121.

The shapes of the ROI objects 41*a*, 41*b*, . . . exemplarily imitate shapes of specific parts or organs, but the operator may set an ROI with a free shape by using the ROI shape designation column 452 of the ROI setting screen 45 illustrated in FIG. 4.

Next, with reference to a flowchart in FIG. 5, a description will be made of flow of a scanning process performed by the X-ray CT apparatus 1.

First, the X-ray CT apparatus 1 performs scanogram scanning under the control of the system control device 124 (step S101). In the scanogram scanning, the system control device 124 performs scanning while relatively moving positions of a subject and the X-ray source 101 by moving the bed in the body axis direction of the subject in a state in which a direction in which X-rays are irradiated is fixed. The scanogram scanning may be performed in either one (single scanogram) of the PA direction and the LAT direction, and may be performed in both (double scanogram) of the PA direction and the LAT direction.

If the scanogram scanning is finished, the image calculation device 122 creates a scanogram image on the basis of transmitted X-ray data obtained through the scanning, and sends the scanogram image to the system control device 124. The system control device 124 displays the acquired scanogram image on the display device 125, and also stores the scanogram image in the storage device 123 (step S102).

Figure 6:
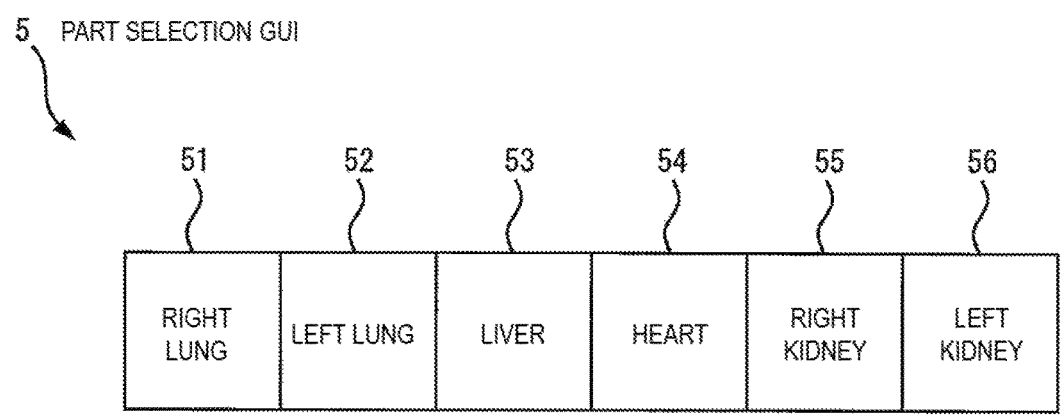
FIG. 6 illustrates an example of a part selection GUI 5.

The system control device 124 displays a part selection GUI 5 when displaying the scanogram image (step S103). FIG. 6 illustrates an example of the part selection GUI 5. As illustrated in FIG. 6, icons 51 to 56 for selecting parts are displayed side by side on the part selection GUT 5. The parts are organs such as the right lung, the left lung, the liver, the heart, the right kidney, and the left kidney.

First, the system control device 124 receives a set scanning range for a scanogram image 3 displayed on the display devise 125 (step S104). The operator used the input device 121 such as the mouse so as to designate the scanning range on the scanogram image 3. The designation of the scanning range is performed by drawing a rectangular frame 33 with a desired size at a desired position on the scanogram image 3 as illustrated in FIG. 7(*a*), for example.

Next, the system control device 124 receives a set ROI on the scanogram image 3 (step S105).

Here, with reference to FIGS. 7 to 9, a description will be made of setting of a scanning range and a reconstruction range through comparison between an example of the related art and the present invention.

In the related art, in a case where a scanning range or a reconstruction range is set, first, as illustrated in FIG. 7(*a*), the setting is performed by disposing the rectangular frame 33 indicating a scanning range for main scanning on the scanogram image 3. In a case where reconstruction conditions are set, the reconstruction conditions may be set by the operator selecting an appropriate scanning protocol from among scanning protocols in which various parameter values included in the reconstruction conditions are predefined.

For example, as illustrated in FIG. 7(b), in a case where the chest is scanned, an operation is performed in which, if the operator is interested in a lung field, the operator selects a scanning protocol in which reconstruction conditions appropriate for a lung field 34 are set, and if the operator is interested in the heart, the operator selects a scanning protocol in which reconstruction conditions appropriate for the heart are set. In recent years, there have been increased cases where a whole body scanned in a single inspection, and a plurality of reconstruction ranges are set for each part.

For example, as illustrated in FIG. 7(c), a process called "multi-reconstruction" may be performed in which a wide scanning range 33 is taken, and a heart 34a, the lung field 34, an abdomen 34b, and a waist 34c are respectively registered as reconstruction ranges in advance. In the reconstruction process called multi-reconstruction, there are a large number of combinations of parts, and thus there is a case in which a scanning protocol is not prepared in advance.

In the present invention, instead of setting a reconstruction range using a rectangular frame, as illustrated in FIG. 2, the ROI objects 41a, 41b, . . . imitating shapes of parts are used. Thus, the part selection GUI 5 as illustrated in FIG. 8(a) is displayed on a display screen displaying a scanogram image, and a part is designated on the part selection GUI 5 so that an ROI object associated with the part is read. The read ROI object is disposed at any position on the scanogram image 3, and thus an ROI is set. As described above, each ROI is associated with each part, and ROI setting information corresponding to each part is set in advance. The ROI setting information includes information such as reconstruction conditions, display parameters, and an application automatically activated after reconstruction.

A detailed description will be made of an operation of setting reconstruction conditions in steps S105 and S106.

As illustrated in FIG. 8(a), if a part of interest (for example, the right lung icon 51) is selected from the part selection GUI 5, the system control device 124 reads the ROI object 41a (right lung ROI) with a shape of the selected right lung from the ROI table 4a, and displays the ROI object on the scanogram image 3 (FIG. 8(b)).

The operator uses the input device 121 such as the mouse so as to adjust a size, a position, and an angle of the right lung ROI 41a. As illustrated in FIG. 8(c), a mouse pointer 8 is moved onto the ROI, a drag operation is performed, and thus the position of the ROI can be moved. Preferably, by dragging a line indicating a shape of the ROI, the size of the entire ROI can be enlarged or reduced, or a part of the shape of the ROI can be deformed.

In a case where double scanogram (both of the PA direction and the LAT direction) scanning is performed, the ROI objects 41a and 41b respectively corresponding to parts are set on the PA direction scanogram image 3 and the LAT direction scanogram image 3b (refer to FIG. 9), and thus ROIs can be set in a stereoscopic manner.

Figure 10:
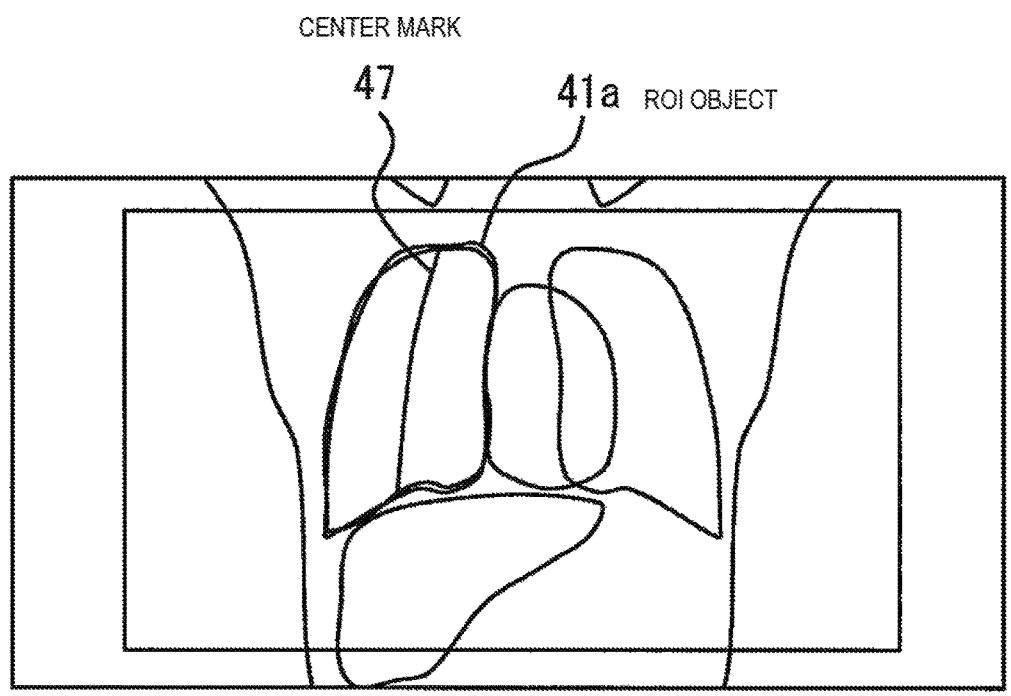

As illustrated in FIG. 10, a center mark 47 is preferably set in the ROI object 41a. The center mark 47 is a mark indicating a center position of the ROI. In an ROI object used for a PA direction scanogram image, the center mark 47 is set, and thus the ROI center (FOV_X) in the X direction (body width direction) can be determined for each slice position. In an ROI object used for a LAT direction scanogram image, the ROI center (FOV_Y) in the Y direction (body thickness direction) can be determined for each slice position.

The system control device 124 may calculate and determine the center mark 47 on the basis of a shape of a ROI object. In other words, a center position from both ends (a left end and a right end (X direction) in the PA direction, and an upper end and a lower end (Y direction) in the LAT direction) of an ROI object at each section position may be set as the FOV center, and the center mark 47 corresponding to a shape of the ROI object may be determined by connecting all FOV center positions at respective section positions in the ROI object.

In a state in which the center mark 47 is not set, as illustrated in FIG. 3, the maximum width of the ROI object may be set as an FOV size, and a central line of the FOV size may be set as the FOV center.

FIG. 5 is described again.

If the ROI is set on the scanogram image 3 by using the part selection GUI 5 and the ROI objects 41, 42, 43, . . . corresponding to respective parts, subsequently, the system control device 124 sets reconstruction conditions corresponding to the set ROI (step S106).

The system control device 124 refers to ROI setting information which is set in advance by the operator and is held in the storage device 124, so as to set respective reconstruction conditions such as a reconstruction filter, a slice thickness, and a slice interval. An image range (a leading image position and a final image position) in the body axis direction, a reconstruction FOV size, the reconstruction FOV center, and the like are set according to the position and the size of the ROI object disposed in step S105.

In a case where the center mark 47 is set when the ROI object is disposed on the scanogram image 3, the FOV centers are respectively set at slice positions along the center mark 47.

Figure 11:
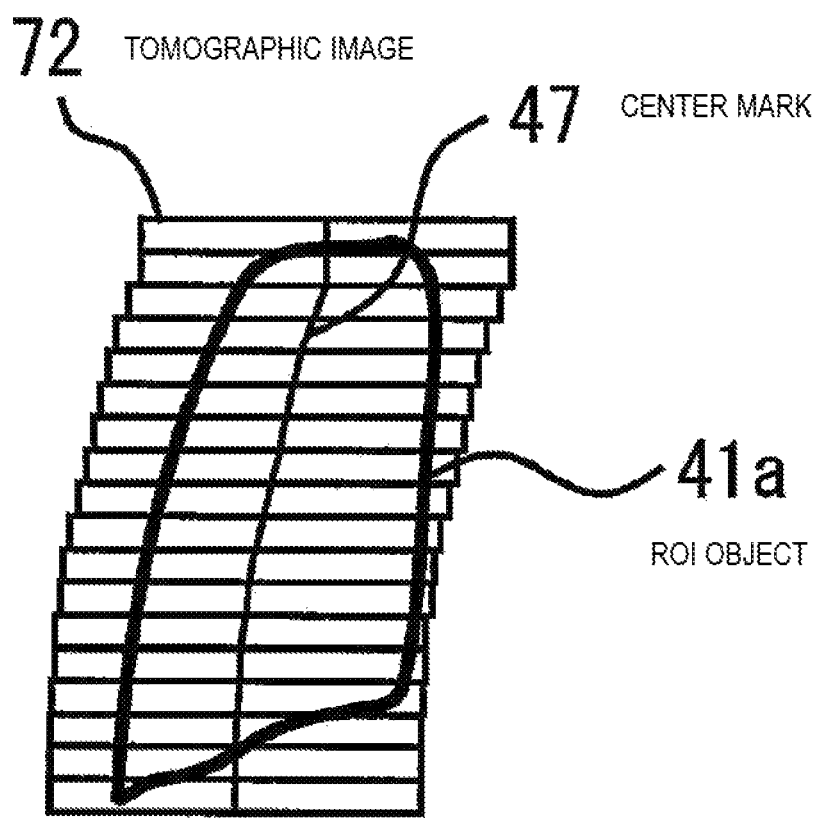
FIG. 11 is a diagram illustrating a relationship between the center mark 47 and the FOV center of each tomographic image 72.

FIG. 11 is a diagram illustrating a relationship between the center mark 47 set in the ROI object 41a and the FOV centers of respective section positions (tomographic images 72).

In the PA direction ROI object 41a illustrated in FIG. 11, the position of the center mark 47 is the FOV center in the X direction in each of the tomographic images 72. A center mark may also be set in a LAT direction ROI object, and a position of the center mark is the FOV center in the Y direction at each section position. In a case of using scanogram images in two directions including the PA direction and the LAT direction, a three-dimensional position of the FOV center at each slice position may be determined by using the center mark of each ROI object.

Figure 12:
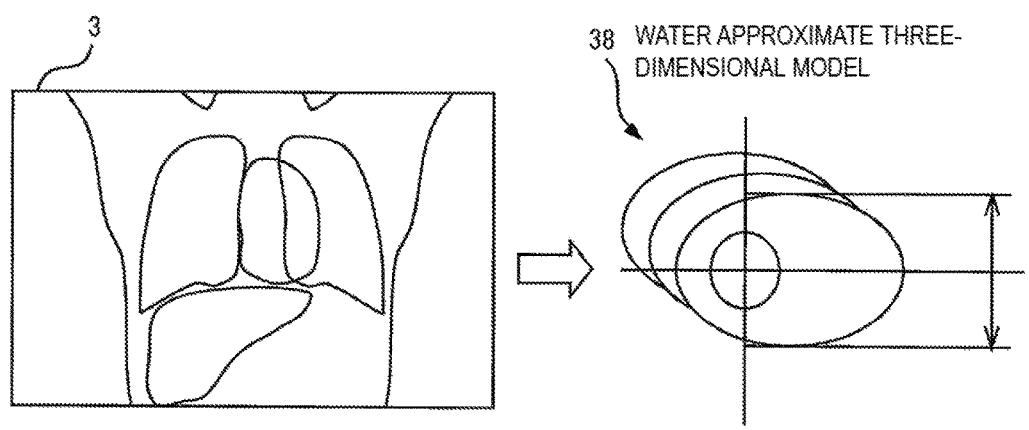
FIG. 12 is a diagram for explaining an example of estimating the FOV center in a Y direction (body thickness direction) by using a water approximate three-dimensional model 38.

In a case where scanogram images from two directions are not acquired, as illustrated in FIG. 12, a water approximate three-dimensional model 38 may be created on the basis of a scanogram image from one direction, and the FOV center (FOV_Y) in the Y direction may be estimated by using the water approximate three-dimensional model. The water approximate three-dimensional model 38 is to convert an X-ray attenuation coefficient in a subject into an X-ray attenuation coefficient in water, and to regard a subject section as an ellipse so as to estimate a major axis and a minor axis thereof. The water approximate three-dimensional model 38 is used for, for example, a dose modulation technique for applying X-rays in an optimal irradiation dose for each X-ray irradiation angle.

In a case where a position of the FOV center in the Y direction is calculated by using the water approximate three-dimensional model 38, it is necessary to set an FOV center position in the Y direction for each part. For example, a center position of a part is defined by using anatomical information such as 30% from the back and 50% from the right body. Consequently, it is possible to calculate a FOV center position in the Y direction on the basis of a thickness (a width in the Y direction) of the water approximate three-dimensional model 38 and a center position of a designated part for each part.

In the processes in steps S105 and S106, as illustrated in FIG. 13(a), a plurality of ROI objects 41a, 43a and 44a may be disposed on the scanogram image 3. In this case, the system control device 124 reads setting information associated with the disposed ROI objects 41a, 43a and 44a, and creates a reconstruction condition table 6 defining reconstruction conditions of each ROI as illustrated in FIG. 13(b). In the example illustrated in FIG. 13(b), a reconstruction condition table defining reconstruction conditions for three parts (ROIs) such as the right lung, the left lung, and the heart is created.

If the reconstruction conditions are set, the system control device 124 starts main scanning (step S107).

During the main scanning, the image calculation device 122 acquires transmitted X-ray data from the scan gantry portion 110, and performs an image reconstruction process (step S108). In the image reconstruction process (image reconstruction process during scanning) in step S108, the entire scanning FOV range is set as a reconstruction FOV. It is preferable to create an image in a reconstruction process in which a calculation amount is small and which can be performed at a high speed, so that the image can be immediately displayed. In the following description, a tomographic image group created with the entire scanning FOV range as a reconstruction FOV will be referred to as the entire image.

The system control device 124 displays the entire image created by the image calculation device 122 in real time, and also displays a scanning position of the currently displayed entire image on the scanogram image (step S109).

Figure 14:
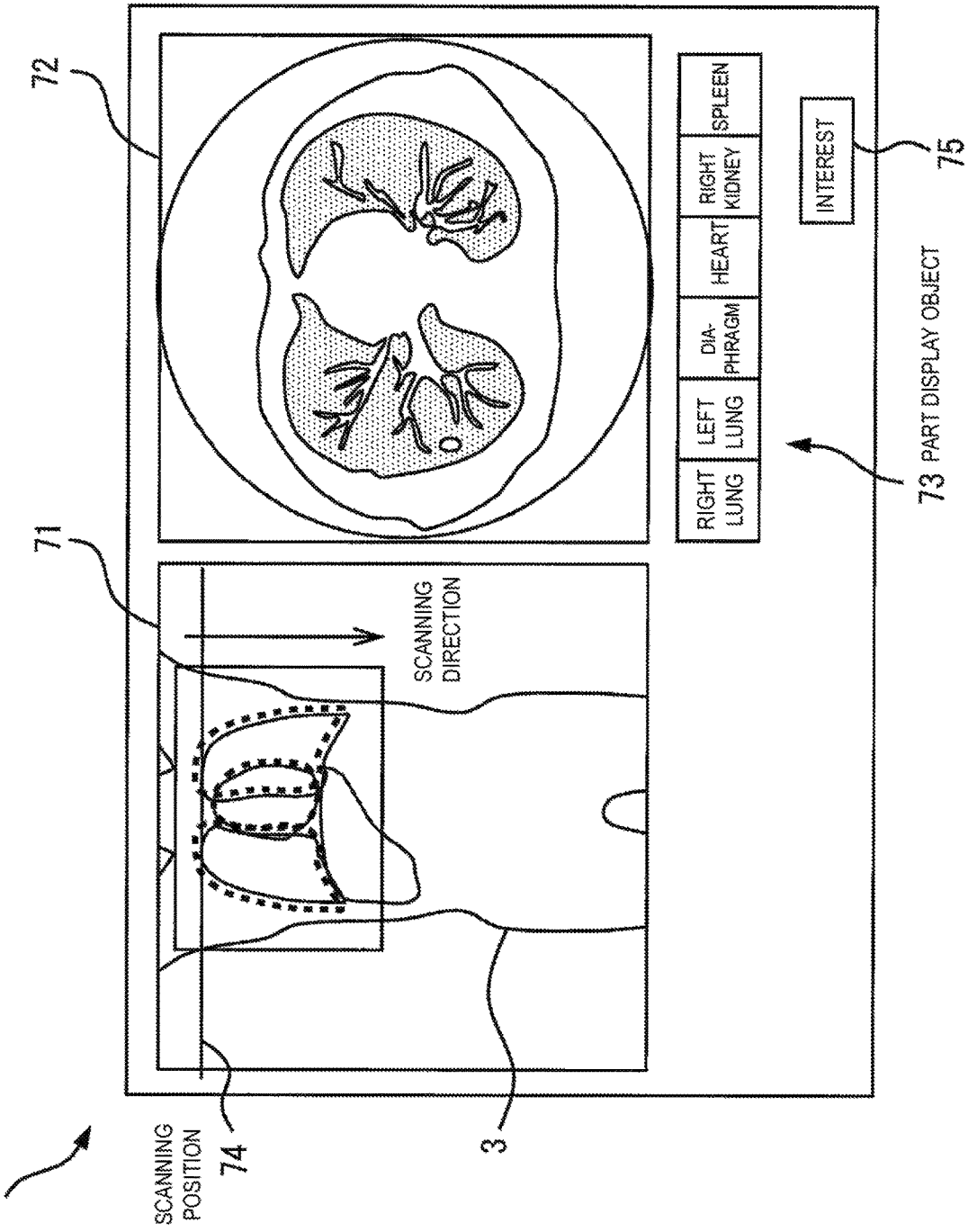
FIG. 14 illustrates an example of a display screen 7 during scanning.

FIG. 14 is a diagram illustrating an example of a display screen 7 during scanning. As illustrated in FIG. 14, a scanogram display region 71 and a tomographic image display region 72 are provided on the display screen 7 during scanning. The system control device 124 sequentially displays the entire image (tomographic images) which is immediately reconstructed after scanning in the tomographic image display region 72. The scanogram image 3 is displayed in the scanogram display region 71, and a line 74 indicating a scanning position is displayed on the scanogram image 3. Consequently, the operator can check a position during scanning and a tomographic image at the position in real time.

In a case where a portion in which an ROI is set is scanned, the system control device 124 preferably displays a notification thereof on the screen so that the operator can visually recognize the notification. For example, as illustrated in FIG. 14, in a case where the system control device 124 displays a part display object 73 in which icons indicating names of respective parts are disposed so as to be arranged, on the display screen 7 during scanning, and a position where an ROI is set is scanned, a notification is performed by highlighting an icon of a scanning position or a part associated with an ROI.

Figure 15:
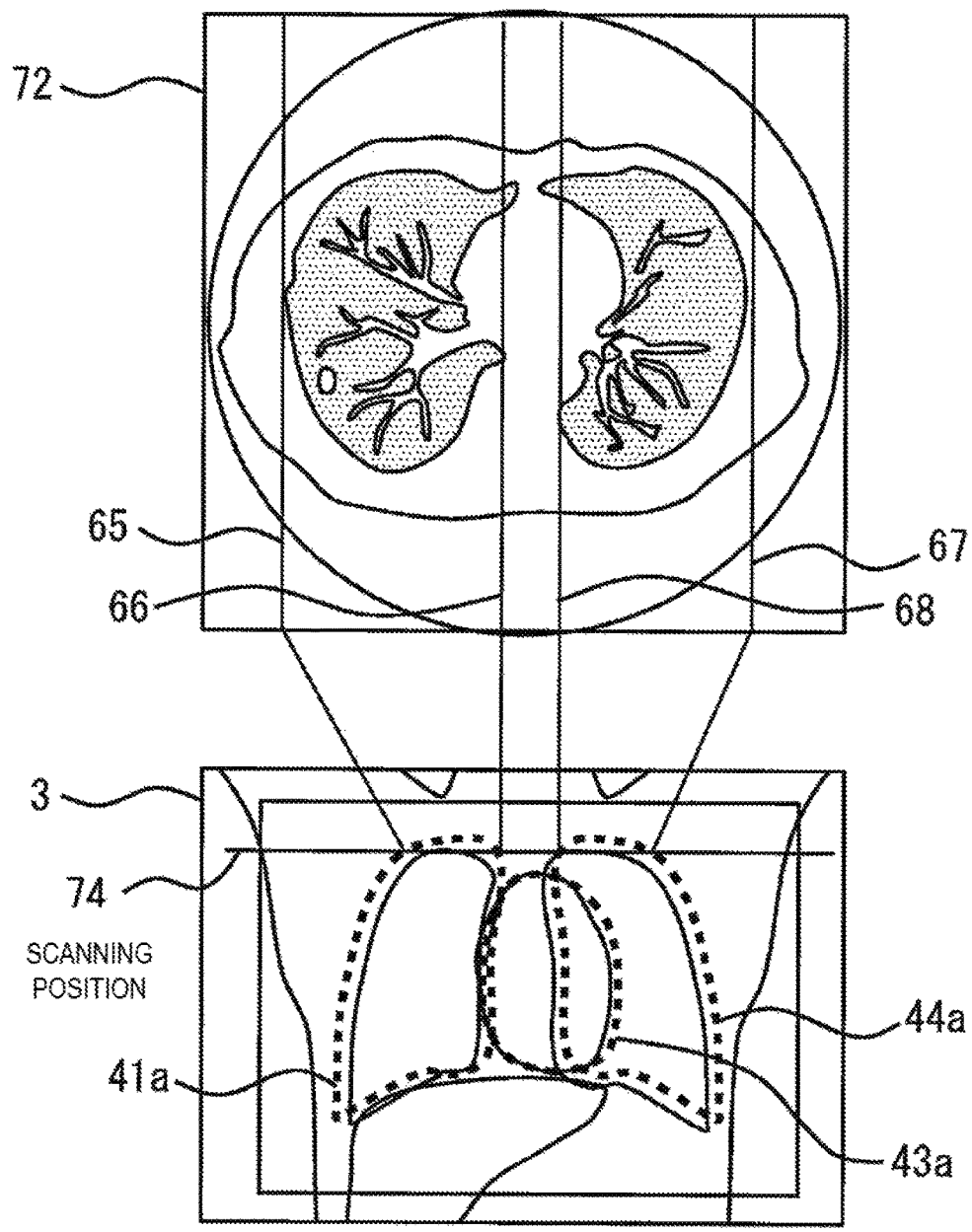
FIG. 15 illustrates another example of a display screen during scanning.

As illustrated in FIG. 15, the tomographic image 72 created through a reconstruction process during scanning may be displayed in real time, and a line or the like indicating a position of an ROI may be displayed on the tomographic image 72.

In an example illustrated in FIG. 15, the ROI 41a and the ROI 44a are set at a position indicated by a line 74. In a case where a scanning position for a currently displayed tomographic image is located at a position indicated by the line 74, a range corresponding to the ROI 41a on the tomographic image is indicated by lines 65 and 66, and a range corresponding to the ROI 44a is indicated by lines 67 and 68.

As illustrated in FIG. 14, an "interest" button 75 may be provided on the display screen 7 during scanning. The "interested" button 75 is a button operated used to add a mark to the displayed tomographic image. By adding a mark to a displayed tomographic image, an image of a position to which the mark is added can be easily read and displayed at any time.

The image calculation device 122 repeatedly performs an image reconstruction process and display of a tomographic image until reaching a scanning end position (step S110; No→step S108, and step S109). If the scanning end position is reached (step S110; Yes), the system control device 124 finished scanning, and performs an image reconstruction process for each ROI under reconstruction conditions which are set to be associated with each ROI in advance (step S111).

In the image reconstruction process in step S111, the image calculation device 122 reconstructs an image (diagnosis image) of each ROI (part) by using reconstruction conditions which are set in advance as ROI setting information. The image reconstructed in step S111 is displayed in a viewing process (step S112) described below.

In a case where an application automatically activated after the image is reconstructed is designated as the ROI setting information, the system control device 124 activates the application, and transitions to a process according to the application.

Figure 5:
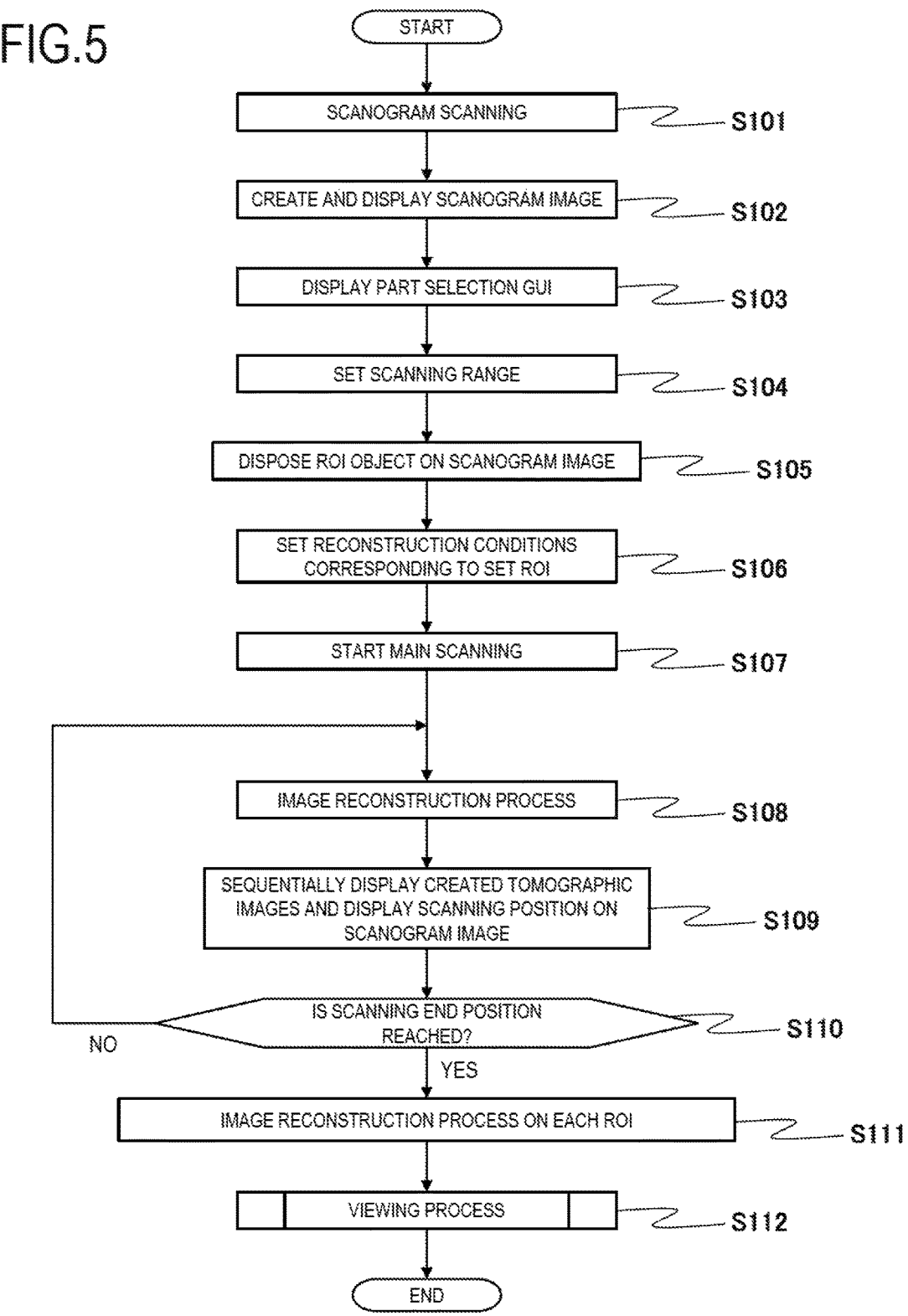
FIG. 5 is a flowchart illustrating a flow of a scanning process.

The flowchart of FIG. 5 shows process procedures in which the entire image of respective slice positions is reconstructed and displayed for checking, and then a diagnosis image of each ROI is reconstructed, but there may be process procedures in which reconstruction and display processes of the entire image for checking are omitted, and a diagnosis image of each ROI is reconstructed and displayed immediately after scanning. Preferably, the reconstruction process procedures can be freely changed through a setting operation of the operator.

The viewing process in step S112 will be described with reference to FIGS. 16 and 17.

FIG. 16 is a flowchart illustrating a flow of the viewing process.

In the viewing process, the system control device 124 displays an image viewing screen 81 (step S201). If the operator designates a part to be viewed on the image viewing screen 81 (step S202), the system control device 124 acquires an image group of the designated part from the storage device 123 (step S203).

Figure 17A:
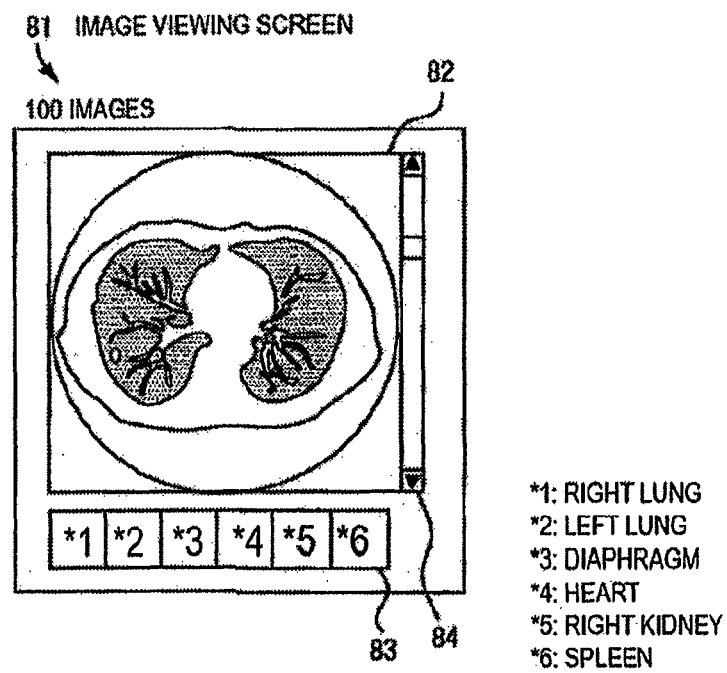
FIG. 17 is a display example of an image viewing screen 81, in which FIG. 17(*a*) illustrates a case where all tomographic images are displayed, and FIG. 17(*b*) illustrates a case where an image is displayed in which a selected part is set as a region of interest.
Figure 17B:
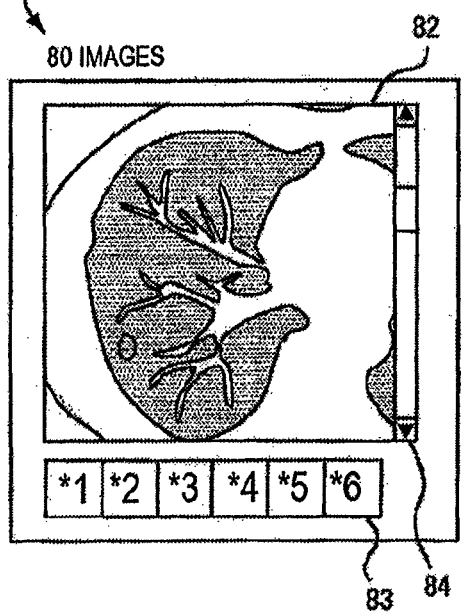

FIG. 17 is a diagram illustrating an example of the image viewing screen 81, in which FIG. 17(a) illustrates an initial display state, and FIG. 17(b) illustrates a state in which a part has been selected.

In step S109 regarding the scanning process illustrated in FIG. 5, for example, in a case where 100 entire images are reconstructed and are stored in the storage device 213, as illustrated in FIG. 17(a), first, tomographic images 82 are displayed one by one on the image viewing screen 81. A scroll bar 84 is operated, and thus the next slice images are sequentially displayed.

If a part selection GUI 83 provided on the image viewing screen 81 is operated, and thus a part to be observed is selected, as illustrated in FIG. 17(b), only diagnosis images of the selected part are extracted from all of the images, and are displayed. The number of displayed images is reduced to, for example, 80. The diagnosis image is an image reconstructed under reconstruction conditions appropriate for the part. Consequently, the operator can easily check an image of a desired part after scanning is finished.

The image viewing process may be performed not only right after scanning is finished, but also at any timing if the entire image and a diagnosis image are created and are stored in the storage device 123.

Figure 18:
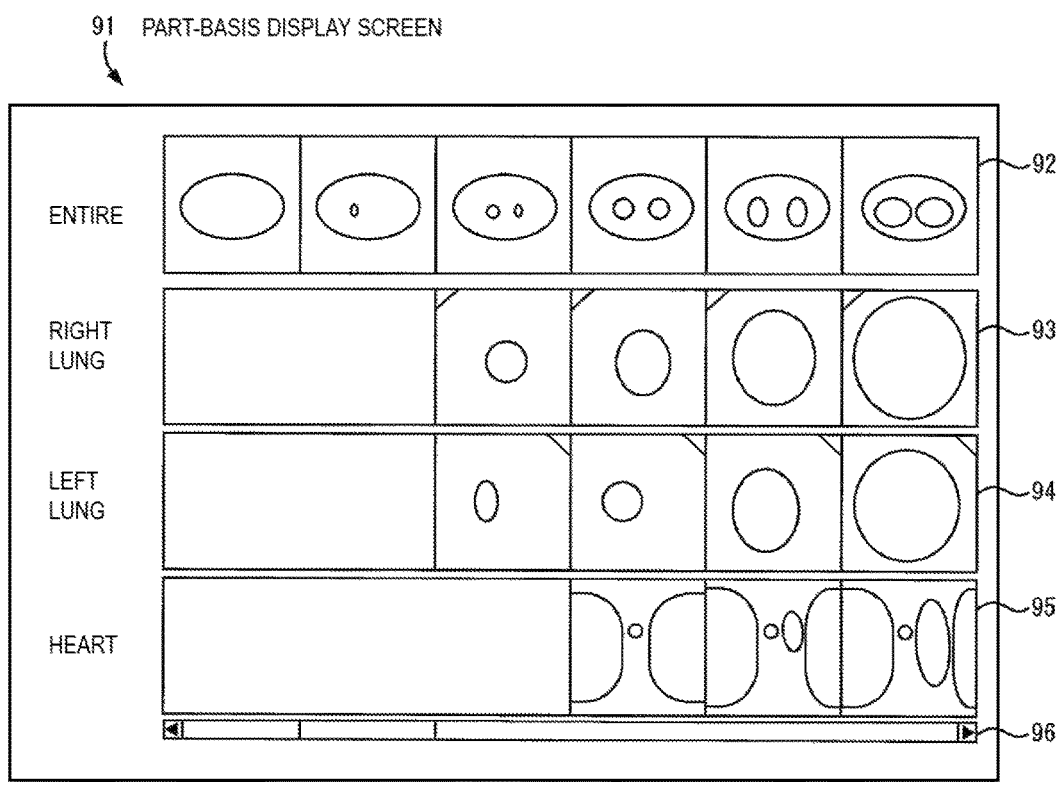
FIG. 18 illustrates an example a part-basis display screen 91.

As illustrated in FIG. 18, the system control device 124 may display images of each part in a list form. In a part-basis display screen 91 illustrated in FIG. 18, a screen transverse direction expresses body axis direction positions, a screen longitudinal direction expresses parts, an entire image group 92 is arranged in the transverse direction so as to be displayed in a list form, and diagnosis images of each part located in the same body axis direction positions are arranged in the longitudinal direction so as to be displayed in a list form. In an example illustrated in FIG. 18, a diagnosis image group 93 of the right lung, a diagnosis image group 94 of the left lung, and a diagnosis image group 95 of the heart are laterally arranged to be displayed under the entire image group 92. A scroll bar 96 is provided on the part-basis display screen 91, and slice images outside the screen can be sequentially displayed by operating the scroll bar.

Consequently, images of a desired section position can be checked for each part while comparing the images with each other after scanning with a simple operation.

Figure 19:
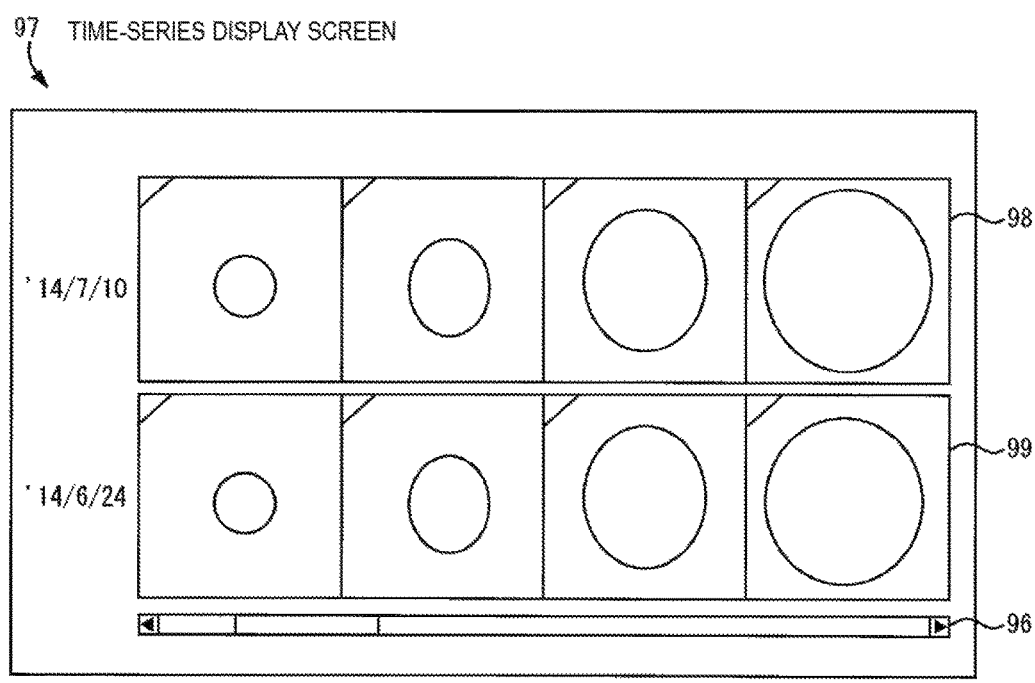
FIG. 19 illustrates an example of a time-series display screen 97.

In a case where the same part (ROI) is inspected (scanned) on another day for the same object, as illustrated in FIG. 19, a time-series display screen 97 on which images are arranged in a time series may be used.

In the time-series display screen 97 illustrated in FIG. 19, a screen transverse direction expresses body axis direction positions, and a screen longitudinal direction expresses the inspection date and time, and the system control device 124 reads respective image groups 98 and 99 in which an ROI is set for the same part, and displays the images in the transverse direction in a list form. In the example illustrated in FIG. 19, the image group 98 scanned on "'14/7/10" and the image group 98 scanned on "'14/6/24" are arranged to be displayed.

A scroll bar 96 is provided on the time-series display screen 97, and slice images outside the screen can be sequentially displayed by operating the scroll bar.

Consequently, it is possible to observe progress of a target part with a simple operation after scanning.

As described above, the X-ray CT apparatus 1 of the present invention holds an ROI object indicating each part in the storage device 123, and receives a set region of interest associated with the part by disposing the ROI object on a scanogram image. The X-ray CT apparatus 1 performs main scanning under conditions associated with the set region of interest (ROI), and reconstructs an image under conditions appropriate for each part on the basis of X-ray information obtained through the main scanning.

Consequently, a part (an organ or the like, that is, a part as a diagnosis target) can be set as a region of interest on a scanogram image which scanned for positioning before main scanning. It is possible to immediately automatically set conditions appropriate for a region of interest and to perform scanning, or it possible to automatically set reconstruction conditions for an image used for diagnosis and to create an image. Consequently, it is possible to rapidly create and display images used for diagnosis from a large number of image groups. A diagnostic reading doctor or the like can extract, display, and read only target diagnosis images with simple operation, and thus it is possible to reduce an amount of work.

Since a shape of an ROI object is a shape corresponding to a part, if an ROI has only to be disposed on a scanogram image, it is possible to immediately set a reconstruction FOV with a size appropriate for the part. If an operator can adjust a shape of an object, it is possible to set an ROI optimal for a subject. Since an operator can set setting information including at least reconstruction conditions for each ROI object, the operator can set setting information so that an appropriate image is created according to the diagnosis content or the operator's taste.

As mentioned above, preferred embodiments of the X-ray CT apparatus according to the present invention have been described with reference to the drawings, but the present invention is not limited to the above-described embodiments. It is clear that a person skilled in the art can conceive of various modifications or alterations within the technical spirit disclosed in the present specification, and it is understood that they are naturally included in the technical scope of the present invention.

REFERENCE SIGNS LIST

1 X-ray CT Apparatus, 100 Scan Gantry Portion, 101 X-ray Source, 102 Rotation Board, 104 Opening, 105 Bed, 106, X-ray Detector, 107 Data Collecting Device, 120 Operation Console, 121 Input Device, 122 Image Calculation Device, 123 Storage Device, 124 System Control Device, 125 Display Device, 3 Scanogram Image (PA Direction), 3b Scanogram Image (LAT Direction), 4a and 4b ROI Table, 41a and 42a ROI object (PA Direction), 41b and 42b ROI object (LAT Direction), 45 ROI Setting Screen, 47 Center Mark, 5 Part Selection GUI, 6 Reconstruction Condition Table, 7 Display Screen during Scanning, 81 Image Viewing Screen, 91 Part-Basis Display Screen, 96 Time-Series Display Screen

The invention claimed is:
1. An X-ray CT apparatus comprising:
an X-ray irradiation unit that irradiates X-rays from each direction around a subject;
an X-ray detection unit that detects X-rays having been transmitted through the subject;
a scanogram image creation unit that creates a scanogram image through scanning while moving relative positions of the subject and the X-ray irradiation unit, in a body axis direction, in a state in which an X-ray irradiation direction is fixed;
a storage unit that holds a plurality of objects that have shapes corresponding to parts indicating diagnosis targets;
a region-of-interest setting unit that sets a region of interest associated with a part, by disposing an object, selected from the plurality of objects, on the scanogram image and sets a reconstruction condition in association with the region of interest set by disposing the object on the scanogram image; and
an image reconstruction unit that performs main scanning, and thereafter reconstructs, on the basis of X-ray information obtained through the main scanning an image including the region of interest under the reconstruction condition set by the region-of-interest setting unit.
2. The X-ray CT apparatus according to claim 1, further comprising:

an operation input unit that inputs an operation of adjusting a shape of the object.

3. The X-ray CT apparatus according to claim 2, wherein a reconstruction field of view range in a slice section is determined on the basis of a shape of the region of interest.

4. The X-ray CT apparatus according to claim 1, further comprising:
a setting information input unit that sets setting information including at least reconstruction conditions for each object in advance,
wherein the image reconstruction unit reconstructs an image on the basis of the setting information.

5. The X-ray CT apparatus according to claim 1, further comprising:
a notification unit that performs a notification of a scanning position or a scanning part in a case where a position including the region of interest is scanned in the main scanning.

6. The X-ray CT apparatus according to claim 1, wherein the image reconstruction unit sequentially reconstructs tomographic images during execution of main scanning, and
wherein the X-ray CT apparatus further includes a display unit that arranges and displays the scanogram image and the tomographic images in real time, and displays scanning positions of the tomographic images on the scanogram image.

7. The X-ray CT apparatus according to claim 6, wherein the display unit displays a position of the region of interest in a case where the region of interest is included in a currently displayed tomographic image.

8. The X-ray CT apparatus according to claim 6, further comprising:
a mark adding unit that adds a mark to a currently displayed tomographic image.

9. The X-ray CT apparatus according to claim 1, wherein the object is associated with information for designating a processing program which is automatically activated after an image is reconstructed, and
wherein the X-ray CT apparatus further includes a program activation unit that activates the processing program after an image is reconstructed.

10. The X-ray CT apparatus according to claim 1, further comprising:
a storage unit that stores a reconstructed image group;
a part selection unit that selects a part; and
an image viewing processing unit that extracts and acquires an image including a selected part from the storage unit, and displays the acquired image under display conditions set for a region of interest associated with the part.

11. The X-ray CT apparatus according to claim 1, further comprising:
a storage unit that stores a reconstructed image group; and
a part-basis display unit that acquires images from the storage unit, and arranges and displays the images for each part.

12. The X-ray CT apparatus according to claim 1, further comprising:
a storage unit that stores a reconstructed image group in correlation with information regarding the date and time at which the image group is scanned; and
a time-series display unit that acquires images of the same patient which are scanned at another date and time and include a specific region of interest from the storage unit, and that arranges and displays the images in a time series.

13. A scanning method for an X-ray CT apparatus which irradiates X-rays from each direction around a subject, and detects X-rays having been transmitted through the subject, the method comprising:
(a) a step of creating a scanogram image through scanning while moving relative positions of the subject, in a body axis direction, in a state in which an X-ray irradiation direction is fixed;
(b) a step of setting a region of interest associated with a part, by disposing an object, selected from a plurality of objects that are registered in a storage device and have shapes corresponding to parts indicating diagnosis targets, on the scanogram image and setting a reconstruction condition in association with the region of interest set by disposing the object on the scanogram image; and
(c) a step of performing main scanning, and thereafter reconstructing on the basis of X-ray information obtained through the main scanning an image including the region of interest under the reconstruction condition set in (b).

* * * * *